United States Patent [19]

Holm

[11] Patent Number: 5,746,979

[45] Date of Patent: May 5, 1998

[54] METHOD FOR RECEIVING AND SEPARATING A FLUID INTO ITS INGREDIENTS

[75] Inventor: Niels Erik Holm, Birkerød, Denmark

[73] Assignee: E. R. Squibb & Sons, Inc., Skillman, N.J.

[21] Appl. No.: 472,039

[22] Filed: Jun. 6, 1995

Related U.S. Application Data

[62] Division of Ser. No. 240,641, May 2, 1994, Pat. No. 5,462,716.

[30] Foreign Application Priority Data

Nov. 11, 1991 [DK] Denmark .................................. 1848/91

[51] Int. Cl.⁶ .................................. G01N 9/30; B01L 3/00; B01D 43/00
[52] U.S. Cl. .................................. 422/72; 422/101; 422/102; 422/103; 436/175; 436/177; 206/509; 383/32; 383/37; 494/36; 494/31; 494/38; 604/4
[58] Field of Search .................................. 422/101, 72, 102, 422/103; 436/69, 175, 177; 435/2; 383/32, 37, 38; 494/31, 36, 38, 41; 128/912; 604/4–6, 9, 319–321; 206/218, 503, 508, 509; 210/252, 261

[56] References Cited

U.S. PATENT DOCUMENTS

| | | | |
|---|---|---|---|
| 3,064,647 | 11/1962 | Earl | 424/529 |
| 3,078,847 | 2/1963 | Wandell et al. | 422/41 |
| 3,223,083 | 12/1965 | Cobey | 606/92 |
| 3,799,342 | 3/1974 | Greenspan | 210/780 |
| 3,870,042 | 3/1975 | Viguier | 604/406 |
| 3,908,893 | 9/1975 | Williams | 494/4 |
| 3,911,918 | 10/1975 | Turner | 604/410 |
| 3,932,277 | 1/1976 | McDermott et al. | 210/780 |
| 3,982,691 | 9/1976 | Schultz | 494/429 |
| 3,986,506 | 10/1976 | Garber et al. | 604/406 |
| 4,086,924 | 5/1978 | Latham, Jr. | 604/6 |
| 4,141,887 | 2/1979 | Seufert | 530/383 |
| 4,300,717 | 11/1981 | Latham, Jr. | 494/41 |
| 4,359,049 | 11/1982 | Redl et al. | 33/17 |
| 4,471,888 | 9/1984 | Herb et al. | 222/137 |

(List continued on next page.)

FOREIGN PATENT DOCUMENTS

| | | |
|---|---|---|
| 514223 | 12/1978 | Australia . |
| 552883 | 6/1986 | Australia . |
| 446713 | 9/1981 | European Pat. Off. . |
| 0446713 | 2/1991 | European Pat. Off. . |
| 0505962 | 3/1992 | European Pat. Off. . |
| 505962 | 9/1992 | European Pat. Off. . |
| 39 20 694 | 1/1991 | Germany . |
| WO 88/02259 | 4/1988 | WIPO . |
| WO 91/17778 | 11/1991 | WIPO . |

*Primary Examiner*—Harold Y. Pyon
*Attorney, Agent, or Firm*—Brinks Hofer Gilson & Lione

[57] ABSTRACT

A method of separating fluid into two or more separable fractions. One container section (2) and the adjacent portion of the other container section are made of solid material, and the two container sections are screwed together. The container sections (1 and 2) have their respective chambers (29 and 30) for receiving their respective fluid ingredients, and these chambers are interconnected through a connecting channel (31) through the abutting portions, at which the container sections (1 and 2) are screwed together. A valve seat (21, 27) is shaped at each end of the connecting channel (31) for each valve member (22, 16) for a sealing closing of the chambers (29, 30) in the separated state of the container sections (1, 2). The valve members (22, 16) have mutually abutting projections (23, 12) ensuring a distance between the valve members (22, 16) exceeding the distance between the associated valve seats (27, 21) in the coupled state of the container sections (1, 2), but being smaller than the distance between the associated valve seats (27, 21) in a position during a separating movement of the container sections (1, 2). Furthermore, retaining means (15, 16) are provided for ensuring that the valve members (22, 16) do not engage the valve seats (27, 21) in the coupled state of the container sections (1, 2).

7 Claims, 5 Drawing Sheets

U.S. PATENT DOCUMENTS

| | | | |
|---|---|---|---|
| 4,530,691 | 7/1985 | Brown | 494/45 |
| 4,566,610 | 1/1986 | Herb et al. | 222/137 |
| 4,596,657 | 6/1986 | Wisdom | 210/206 |
| 4,608,178 | 8/1986 | Johansson et al. | 210/744 |
| 4,666,429 | 5/1987 | Stone | 604/83 |
| 4,668,399 | 5/1987 | Duggins | 210/637 |
| 4,714,457 | 12/1987 | Alterbaum | 494/37 |
| 4,729,829 | 3/1988 | Duggins | 210/195.2 |
| 4,735,616 | 4/1988 | Eibl et al. | 604/191 |
| 4,735,726 | 4/1988 | Duggins | 210/637 |
| 4,767,396 | 8/1988 | Powers | 494/60 |
| 4,769,150 | 9/1988 | Ramstack | 210/636 |
| 4,784,157 | 11/1988 | Halls et al. | 128/762 |
| 4,795,441 | 1/1989 | Bhatt | 604/124 |
| 4,810,378 | 3/1989 | Carmen et al. | 210/206 |
| 4,818,386 | 4/1989 | Burns | 210/97 |
| 4,828,716 | 5/1989 | McEwen et al. | 210/740 |
| 4,856,533 | 8/1989 | Anraku et al. | 128/763 |
| 4,902,281 | 2/1990 | Avoy | 604/191 |
| 4,902,286 | 2/1990 | Ranoux | 604/403 |
| 4,934,827 | 6/1990 | Taschke et al. | 366/162 |
| 5,024,613 | 6/1991 | Vasconcellos et al. | 604/4 |
| 5,030,215 | 7/1991 | Morse et al. | 604/410 |
| 5,100,372 | 3/1992 | Headley | 494/41 |
| 5,137,181 | 8/1992 | Keller | 222/134 |
| 5,318,782 | 6/1994 | Weis-Fogh | 424/529 |
| 5,462,716 | 10/1995 | Holm | 422/102 |
| 5,480,378 | 1/1996 | Weis-Fogh et al. | 604/5 |

METHOD FOR RECEIVING AND SEPARATING A FLUID INTO ITS INGREDIENTS

This application is a division of application Ser. No. 08/240,641, filed May 2, 1994, now U.S. Pat. No. 5,462,716.

TECHNICAL FIELD

The invention relates to a container for receiving and separating a fluid, preferably blood plasma, into its ingredients, where said container comprises two sealingly coupled sections.

BACKGROUND ART

It is known inter alia from U.S. Pat. No. 4,714,457 to utilize the plasma fraction in blood for the preparation of so-called tissue glue. According to the publication the coagulation factors, such as fibrinogen, fibronectin, factor VIII, and factor XIII are precipitated from the plasma fraction. These coagulation factors are precipitated for instance by cryoprecipitation or by means of a precipitation-promoting agent such as ethanol. The precipitated precipitate includes mainly fibrinogen and is used as tissue glue, such as in connection with operation wounds, by the addition of a suitable enzyme, such as thrombin. Like in nature, the fibrinogen and thrombin form together fibrin, which is an insoluble network of fibre-like material constituting a kind of tissue glue interconnecting the wound surfaces during a healing process. On account of the latter effect, a concentrate of coagulation factors containing mainly fibrinogen turned out to possess a favourable effect on the healing process after an operation. For short, the concentrate of coagulation factors is below referred to as fibrinogen, as said fibrinogen is the main ingredient thereof.

Several methods are today used for separating plasma from blood. The separating process can be performed by means of filters or centrifuging techniques or by way of combinations thereof. The methods are usually known as "plasmapheresis". The methods have been developed because it is often sufficient to give the patients a plasma transfusion, whereby it is unnecessary also to remove slowly regenerating blood cells from the donor.

The precipitation of fibrinogen from plasma has previously been performed in closed bag systems. The precipitation into such bags (blood bags) necessitated production of particular means for securing the bags in a centrifugal bowl, in which the centrifuging is to be performed. In addition, it is difficult to separate the fibrinogen from the plasma in a reliable manner. The flexibility of the blood bags often results in the viscous fibrinogen loosening from the bag and mixing with the remaining plasma in the bag, whereby the concentration is substantially reduced. The latter problems have had the effect that these methods are not used by way of routine today.

DESCRIPTION OF THE INVENTION

The container according to the present invention is characterised in that at least one container section and the adjacent portion of the other container section are made substantially of solid material, that the two container sections can be separated, whereby the sections remain sealingly connected during the separating movement away from one another, that the container sections comprise their respective chamber for receiving their respective fluid ingredient, that the chambers are interconnected through a connecting channel defined by mutually abutting portions of each container section, that a valve seat is shaped at each end of the connecting channel for each valve member for a sealing closing of the chambers in the separated state of the container sections, that the valve members comprise mutually abutting projections ensuring a distance between the valve members exceeding the distance between the associated valve seats in the coupled state of the container sections, but being smaller than the distance between the associated valve seats in a position during the separating movement of the container sections, and that retaining means are provided for ensuring that the valve members do not engage the valve seats in the coupled state of the container sections.

The resulting container is well-suited for use during the precipitation of fibrinogen from plasma. In addition, the container allows a sterile storing of the two separated fractions in their respective separate container section. In this manner, the fibrinogen can be stored separately in a refrigerator until it is heated to liquid state immediately before its use and transferred to a syringe so as to be used as tissue glue. The suitability of the container is partly due to the fact that one container section is made of solid material, whereby the fibrinogen can be precipitated on a solid bottom, and partly due to the fact that the container sections can be separated and are automatically closed during the separating movement, whereby the plasma and the fibrinogen are easily placed in their respective container section. As the distance between the valve members is smaller than the distance between the valve seats in a position during the separating movement of the container sections, the valve members close the openings into each container section before said container sections are completely separated during the last step of the separating movement. In this manner, the sealing closing of the container sections can be performed automatically without rendering it possible to handle the container in an incorrect manner.

According to the invention the projections of the valve members may comprise co-operating and releasable snapping means ensuring that the valve members remain coupled together in the coupled state of the container sections. In this manner, a predetermined resistance is ensured against a separation of the valve members during the separating movement of the container sections in such a manner that the valve members are caused to engage their respective valve seats under a predetermined load, whereby said valve members can enter the engagement by way of friction and be retained in said engagement with the valve seats by the friction. In addition, one valve member can be supported at a distance from the associated valve seat by means of the other valve member and retaining means associated therewith.

The retaining means may according to the invention advantageously comprise a retaining projection placed at least on one valve member, said retaining projection extending away from the other valve member and engaging by way of friction adjacent portions of the corresponding container section.

The valve members may according to the invention be associated with their respective biased spring adapted to press said valve members into a sealing engagement with the valve seats during the separation of the container sections. In this manner, an additional pressing force is ensured for the valve members against the valve seats during and after the separating procedure.

According to the invention the retaining projection on at least one valve member may advantageously comprise a recess for a co-operation by way of friction with a projection on the wall of the corresponding container section opposite the valve seat.

Moreover according to the invention the container sections may be coupled together by means of co-operating threads, whereby the coupling and separation of the container sections can be performed in a particularly simple manner.

Furthermore according to the invention, means may preferably be provided for feeding fluid into the container under sterile conditions and for removing fluid ingredients also under sterile conditions from at least one of the separated container sections through the wall thereof. As a result it is possible to remove especially the fibrinogen from the container section in question without opening the valve.

Finally according to the invention the opposing projections of the valve members may comprise a recess on one projection, said recess telescopically receiving the other projection, and the snapping means may be formed by a circumferential rib placed on one projection and engaging a circumferential groove on the other projection with the result that the valve members are retained relative to one another in a particularly simple manner.

BRIEF DESCRIPTION OF THE DRAWINGS

The invention is described in greater detail below with reference to the accompanying drawings, in which.

BEST MODE FOR CARRYING OUT THE INVENTION

Figure 1:
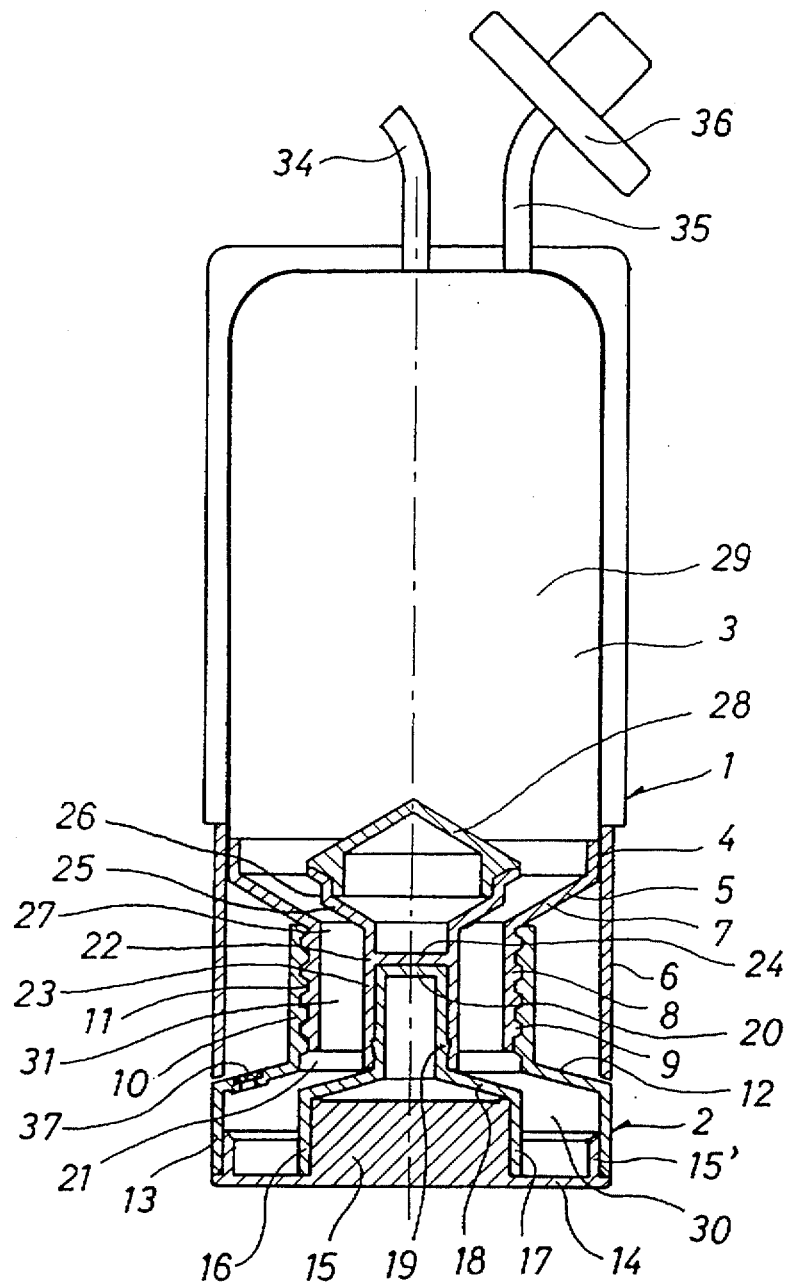
FIG. 1 is a side and substantially sectional view of a container according to the invention.

The container of FIGS. 1 to 4 comprises two container sections designated by the general reference numerals 1 and 2. The upper container section 1 comprises a conventional bottomless blood bag 3, cf. FIG. 1, welded at the lower open end 4 between a rotationally symmetrical mouth portion 5 abutting the inner side of the blood bag 3 and a sleeve-shaped tube portion 6 abutting the outer side of said blood bag. The mouth portion 5 continues through a shoulder portion 7 into a tubular portion 8 provided with a thread 9 on the outside.

The lower second container section 2 is screwed on the thread 9 of the mouth portion 5, cf. the drawing. The entire lower container section 2 is rotationally symmetrically shaped and comprises a tubular portion 10 provided with an internal thread 11. The internal thread 11 engages the thread 9 on the upper container section. The tubular portion 10 continues through a shoulder portion 12 into a cylindrical portion 13. The free end of the cylindrical portion is closed by means of a bottom member 14. The bottom member 14 comprises a disk with a circumferential flange 15' abutting the inner side of the cylindrical portion 13. The bottom member comprises furthermore a central, rotationally symmetrical projection 15 projecting into the interior of the second container section 2. A first valve member 16 is retained on the latter projection by way of friction, said valve member also being rotationally symmetrically shaped.

The first valve member 16 comprises a tubular portion 17 engaging the projection 15 on the bottom member 14. The cylindrical portion continues into a conical portion 18 in turn continuing into a comparatively narrower cylindrical portion 19. The cylindrical portion 19 forms a projection of the valve member 16. The projection 19 is narrower than the cylindrical portion 17 engaging the projection 15 of the bottom member 14. Along the transition area between the broad cylindrical portion 17 and the conical portion 18, the first valve member 16 is adapted to co-operate sealingly with the adjacent inner side of the threaded tubular portion 10 on the lower container section 2. Thus the area in question of the inner side of the tubular portion 10 forms a valve seat 21 for the first valve member. The valve seat 21 and the valve member 16 are besides formed in such a manner that they co-operate with one another by way of friction.

A second valve member 22 is telescopically received on the narrow projection 19 of the first valve member 16. Thus the second valve member 22 comprises a cylindrical projection 23 surrounding the projection 19 on the first valve member 16. Internally, the cylindrical projection 23 comprises a transverse wall 24. Like the first valve member 16, the second valve member 22 comprises a conical portion 25 expanding in a direction away from the projection 23 at the end farthest from the valve member 16 and ending at a cylindrical portion 26. The transition area between the conical portion 25 and the cylindrical portion 26 is adapted to co-operate in a sealing manner with the inner side of the mouth portion 5 of the upper container section 1 on the inner side of the threaded tubular portion 8 of said mouth portion. The portion in question of the mouth portion forms thus a valve seat 27 for the second valve member 22. The valve seat 27 and the valve member 22 are adapted to co-operate with one another by way of friction.

The end of the second valve member 22 facing the interior of the blood bag 3 is closed by means of a conical cap 28 glued thereon.

Figure 2:
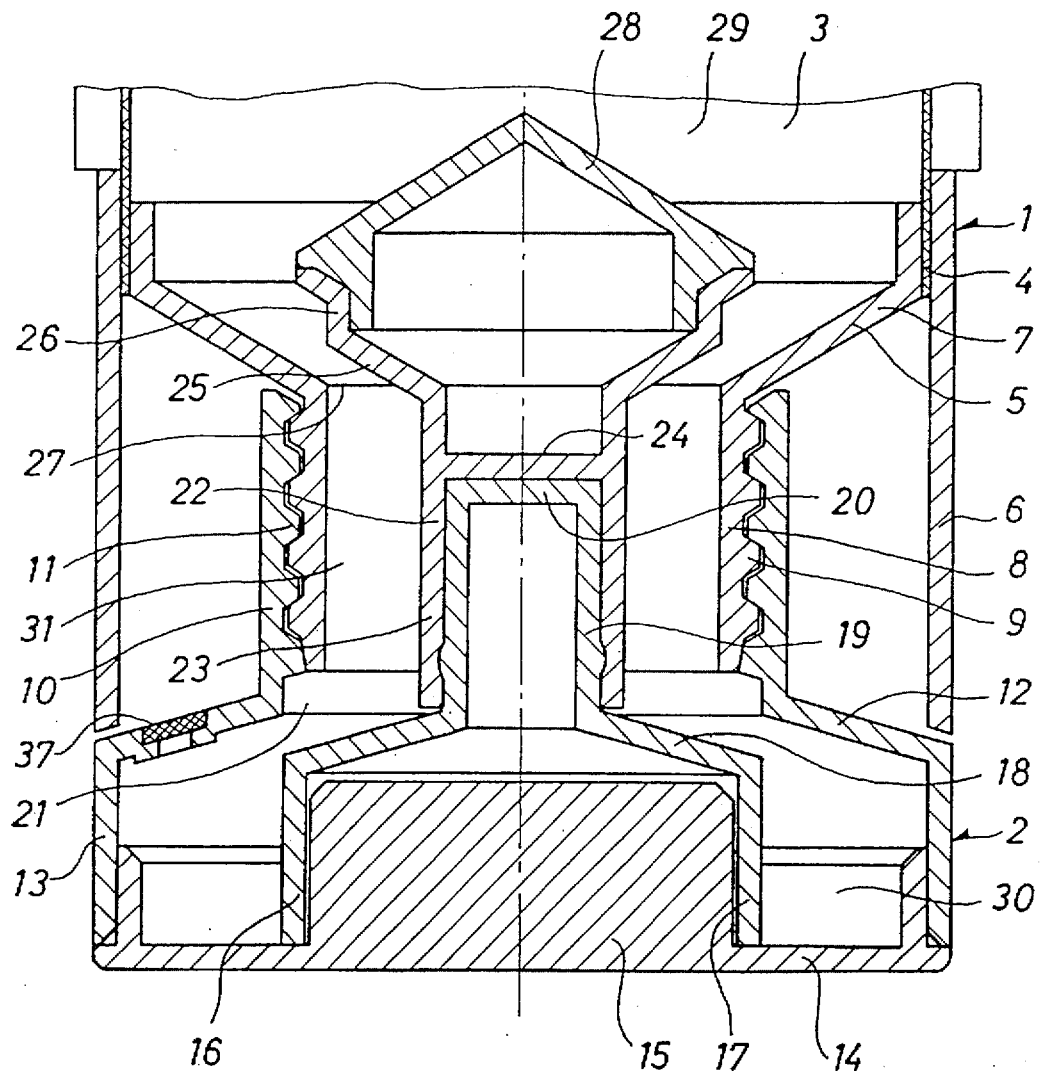
FIG. 2 illustrates on a larger scale the lower portion of the container of FIG. 1, FIG. 3 corresponds to FIG. 2, but in a position during the separating movement of the two sections of the container, FIG. 4 corresponds to FIG. 2, but illustrating the two completely separated container sections.

As illustrated in the drawing, the telescopically co-operating projections 19 and 23, respectively, of the two valve members 16 and 22 are of such a length that the two valve members 16 and 22 in the position shown in FIGS. 1 and 2 are retained inside their respective container section 2 and 1 at a distance from the associated valve seats 21 and 27, said valve members in FIGS. 1 and 2 being supported by the projection 15 on the lower container section 2. As a result, an open connection exists between the interiors of the two container sections 1 and 2. Thus an open connection exists between a first chamber 29 inside the upper container section 1 and a chamber 30 inside the lower container section 2 through a connecting channel 31. The connecting channel 31 is defined by the tubular portions 8 and 10, respectively, of the two container sections 1 and 2. As clearly illustrated in FIG. 4, the projection 19 on the first valve member 16 comprises a circumferential rib 32. Correspondingly, the projection 23 on the second valve member 22 comprises on the inner side a circumferential groove 33. The rib 32 and the groove 33 are adapted to snap-engage one another in such a manner that the second valve member 22 remains positioned on the first valve member 16 in the position of FIG. 1 and is only released by a predetermined force in the axial direction thereof.

Figure 3:
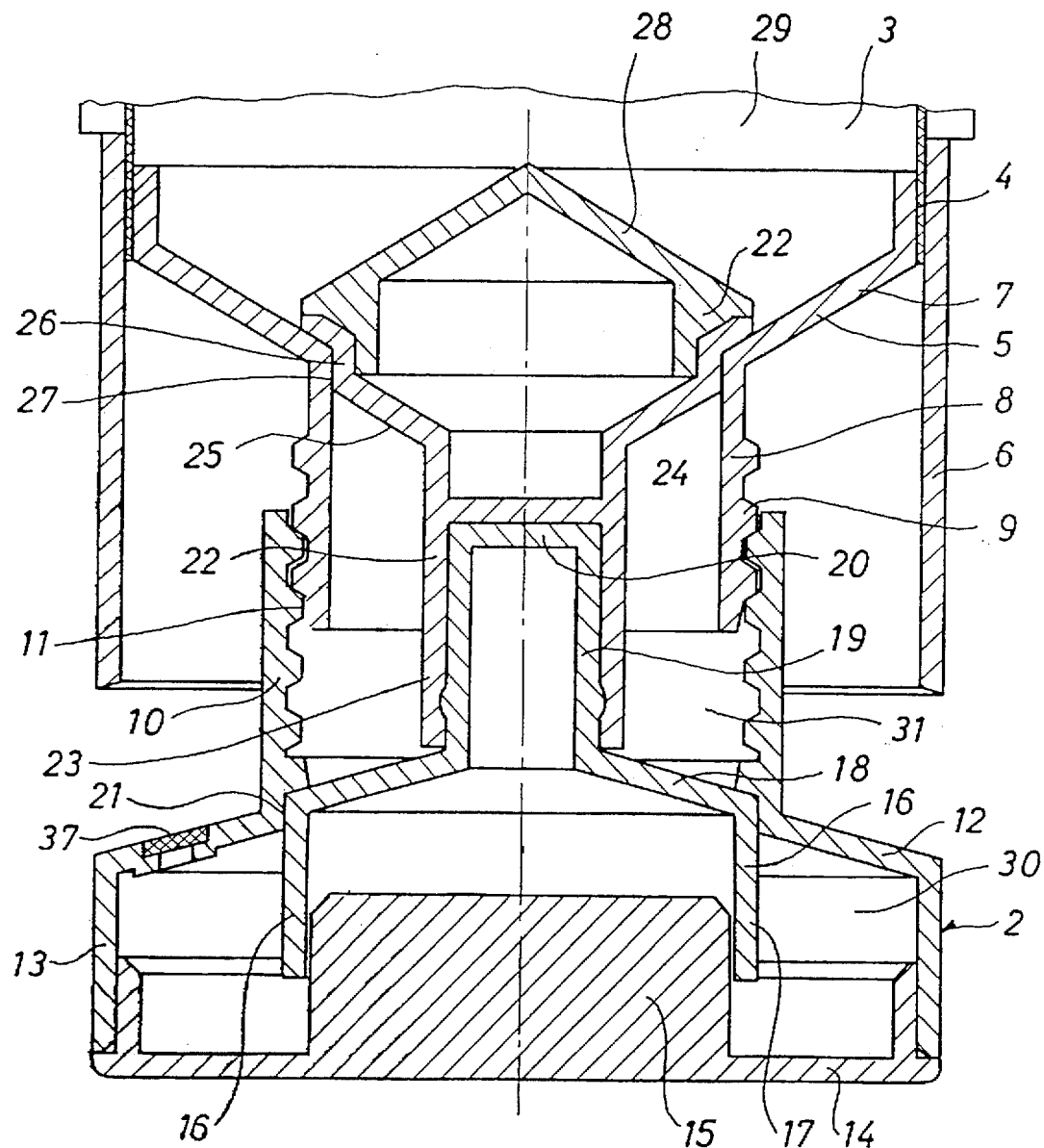

The distance between the two valve members 16 and 22 in the engaging position of the rib 32 and the groove 33 is of such a size, cf. FIG. 3, that the valve members 16 and 22 engage their associated valve seats 21 and 27, respectively, when the two container sections 1 and 2 have been partially unscrewed from one another, but are still engaging one another through their threads 9 and 11. As also illustrated in FIG. 3, the first valve member 16 is partially disengaging the projection 15 on the bottom portion 14 of the lower container section 2 in the position in which the valve members 16 and 22 have fully engaged their valve seats 21 and 27. The engagement of the valve members 16 and 22 by means of the rib 32 and the groove 33 has the effect that the valve members 16 and 22 remain coupled together until they have been pulled into position relative to their valve seats 21 and 27.

Figure 4:
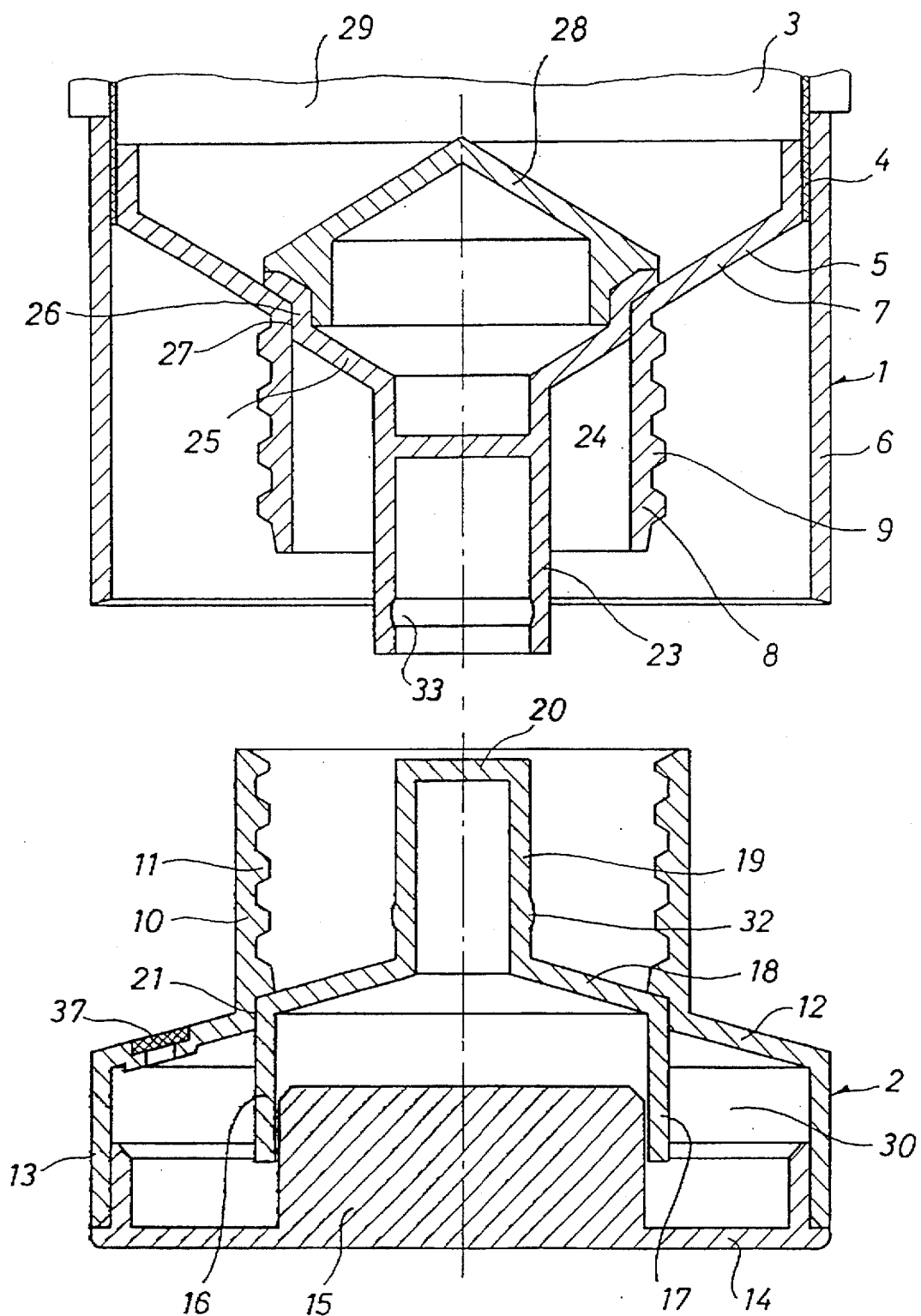

A continued unscrewing of the two container sections 1 and 2 relative to one another has the result that the two valve members 16 and 22 are pulled out of their engagement, cf. FIG. 4, and left sealingly engaging their respective valve seats 21 and 27.

As illustrated in the drawing, the first container section comprises a tubing 34 for the feeding of plasma to the first container section 1. The container section comprises furthermore a tubing 35 allowing feeding under sterile conditions through a conventional filter of an agent, such as alcohol, for instance ethanol, for an acceleration of the precipitation of a concentrate of coagulation factors in the container.

A rubber membrane 37 is furthermore provided within the shoulder portion 12 on the second container section, said rubber membrane allowing exsuction of concentrate from the second container section 2 by means of a syringe.

Beyond assisting in fastening the blood bag 3 on the mouth portion 5 of the upper container section 1, the outer sleeve-shaped tube portion 6 serves also to provide the container with a pleasant appearance, said tube portion 6 abutting the broad cylindrical portion 13 on the second container section 2 when the two container sections are screwed tightly together.

When the container according to the invention is used, plasma is filled therein through the tubing 34. After addition of suitable agents for accelerating the precipitation of coagulation factors, the precipitation process is initiated in a conventionally known manner, such as by way of cryoprecipitation. Subsequently, the container is subjected to a centrifuging in such a manner that the very viscous concentrate is placed in the second chamber 30 of the container inside the second container section 2. When the concentrate has been collected in the second container section 2, the container is turned in such a manner that the container section 1 with the blood bag 3 faces downwards. As a result, the blood plasma flows into the blood bag 3 while the concentrate of fibrinogen or coagulation factors remain in the container section 2 now being the upper section. Then the two container sections 1 and 2 are separated by being unscrewed from one another. As the two container sections gradually reach the position shown in FIG. 3 during their separating movement, the two valve members 16 and 22 are pulled into a tight engagement with their respective valve seats 21 and 27. A continued unscrewing during the last step of the mutual separating movement of the two container sections causes the two valve members 16 and 22 to be pulled out of their engagement. Finally, the two container sections 1 and 2 reach the completely separated state shown in FIG. 4, said state allowing the sections to be handled separately according to desire. The container section 2 containing the concentrate can be placed in an refrigerator until the concentrate is to be used. When the concentrate is to be used, it is heated until it is sufficiently liquid for being sucked out through the rubber membrane 37.

Figure 5:
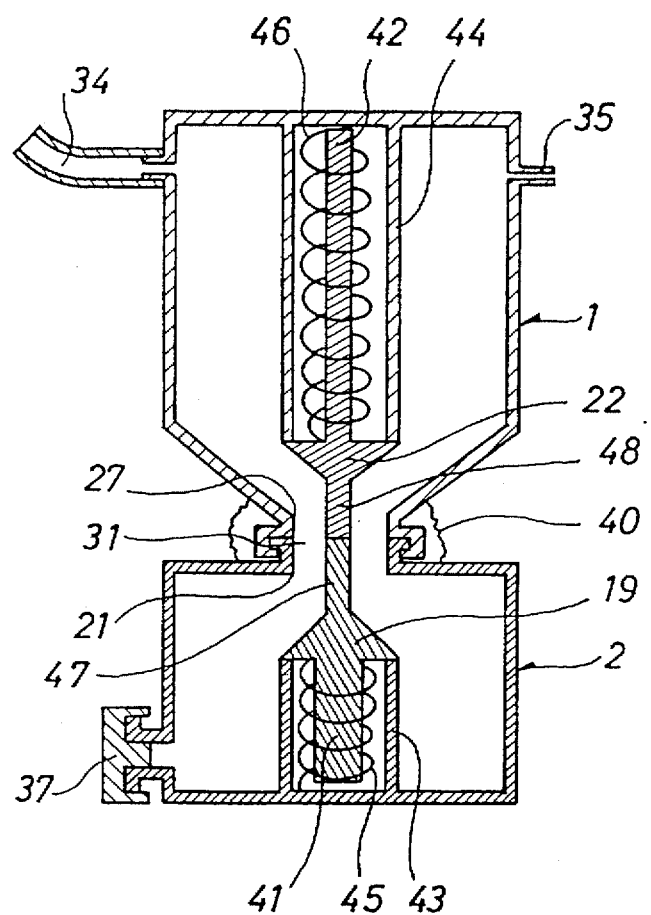
FIG. 5 is a diagrammatic, sectional view of another embodiment of a container according to the invention.

FIG. 5 is a diagrammatic view of a second embodiment of the invention, where parts corresponding to the embodiment of FIGS. 1 to 4 have been provided with the same reference numerals. The container of FIG. 5 comprises also two container sections 1 and 2. These container sections 1 and 2 are screwed together by means of a short thread. Therefore, a sterile-closing membrane 40 is provided about the connection place, said membrane being diagrammatically indicated. The membrane 40 is broken when the two container sections 1 and 2 are pulled a short distance apart after having been unscrewed from one another. Each container section 1 and 2 comprises a valve member 19 and 22 co-operating with their respective valve seat 21 and 27. Both valve members 19 and 22 comprise projections 41 and 42 facing away from their valve seats, said projections being received in their respective guide tubing 43 and 44, respectively. A spring 45 and 46 is arranged about each projection 41 and 42, said springs biasing the valve members 19 and 22 forwards towards their valve seats 21 and 27. The valve members 19 and 22 comprise furthermore projections 47 and 48 projecting forwards towards one another and abutting one another in the position shown in FIG. 5 so as to keep the valve members 19 and 22 in contact with the ends of the guide tubings 43 and 44 at a distance from the valve seats 21 and 27. The separation of the two container sections 1 and 2 activates the springs 45 and 46 to press the valve members against their respective valve seats 21 and 27, the two abutting projections 47 and 48 being of such a length that the valve seats engage one another before the membrane 40 is broken.

The embodiment of the container shown in FIG. 5 is used in the same manner as stated above.

The container according to the invention is easily produced from injection moulded parts, and as far as the embodiment of FIGS. 1 to 4 is concerned the two valve members 16 and 22 are assembled before the blood bag 3 is glued onto the mouth portion 5. Before the second valve member 22 is secured to the first valve member 16, said first valve member is mounted on the projection 15 on the bottom member 14, which is subsequently glued onto the second container section 2. The blood bag 3 is, as mentioned, fastened by way of gluing, but it can also be fastened by way of welding. Both the second container section 2 and the valve members 16 and 22 as well as the mouth portion 5 of the first container section 1 and the sleeve-shaped tube portion 6 are made of a solid plastic material, which may be of any suitable nature, such as polyvinyl chloride.

The invention has been described with reference to preferred embodiments. Many modifications may, however, be carried out without thereby deviating from the scope of the invention. The container of FIGS. 1 to 4 may for instance be of another shape than the rotationally symmetrical shape. Suitable sealing means may furthermore be provided in order to ensure the necessary sealing. The described container is preferably intended for use in connection with blood plasma, but it may, of course, also be used for other fluids with ingredients available in states allowing the described separation.

I claim:

1. A method of separating fluid into two or more separable fractions, comprising the steps of:
    providing a container having at least a first and a second chamber which are separably joined by cooperating connectors proximate an opening in each of said chambers and in fluid communication when joined;
    admitting a fluid into at least one of said first and second chambers;
    providing a closure for selectively sealing the opening in at least one of said first and second chambers;

causing said closure to be open to permit fluid communication between said first and second chambers through a channel when said first and second chambers are joined and centrifuged;

centrifuging the container and fluid to cause a first separable fraction to accumulate preferentially in one of said first and second chambers;

accumulating a substantial portion of the remaining separable fractions in the other of said first and second chambers;

selectively sealing the opening in at least one of said first and second chambers after said centrifugation but before said chambers are separated by causing said closure to seat and close said channel when said cooperating connectors are moved apart; and thereafter separating said chambers; wherein said step of selectively sealing the opening in at least one of said chambers is accomplished automatically as the chambers are being separated but before the interior of the sealed chamber is exposed to an external environment.

2. The method of claim 11 wherein both said first and second chambers are automatically sealed by closures.

3. A method of separating plasma into two or more components, comprising the steps of:

introducing plasma into a chamber of a container having at least a first and second chamber which are separably joined and in sterile fluid communication through a channel when joined, wherein a first of said chambers comprises a flexible bag and a second of said chambers is substantially rigid;

treating said plasma in order to precipitate at least one plasma component;

centrifuging the container and plasma to cause said at least one plasma component to accumulate preferentially in said substantially rigid chamber;

accumulating a substantial portion of the remaining plasma in said flexible bag;

sealing at least said substantially rigid chamber while its interior remains isolated from contaminating environments through use of a closure located within said channel said closure including a valve body which is caused to seat and close said channel when said rigid chamber and said flexible bag are moved apart; and thereafter separating said chambers.

4. The method of claim 3 wherein the plasma is treated with a precipitating agent in order to precipitate said at least one plasma component.

5. The method of claim 3 further comprising the step of removing at least a portion of said at least one plasma component from said substantially rigid chamber through a wall of a chamber.

6. The method of claim 3 wherein both of said chambers are sealed while the chamber interiors remain isolated from contaminating environments.

7. A method of separating a fluid mixture into two or more components, comprising the steps of:

providing a container having a first section defining a first chamber and a second section defining a second chamber, with a channel between said chambers through which fluid can pass between said chambers when said first and second sections are in a coupled condition, said channel having two ends;

providing a valve mechanism for closing each end of said channel, said valve mechanism having a valve adapted to close a respective end of said channel and a spacing member engaging said valves, said spacing member separating said valves and spacing said valves from closing said channel in said coupled condition, whereby said channel is open to fluid communication between said chambers;

admitting a fluid mixture into at least one chamber of said container;

centrifuging said container to cause a first fluid fraction of said fluid mixture to accumulate preferentially in said first chamber;

pulling said first and second sections away from each other in a manner to first cause said valves to close each respective end of said channel, and then to exceed a length of said spacing member such that said sections are in an uncoupled condition with said chambers closed.

* * * * *

UNITED STATES PATENT AND TRADEMARK OFFICE
CERTIFICATE OF CORRECTION

PATENT NO. : 5,746,979
DATED : May 5, 1998
INVENTOR(S) : Niels Erik Holm

It is certified that error appears in the above-identified patent and that said Letters Patent is hereby corrected as shown below:

Under [73] Assignee, change "F. R. Squibb & Sons, Inc." to -- E. R. Squibb & Sons, Inc. --.

Under "Foreign Patent Documents," change "505962  3/1992  European Pat. Off." To -- 505962  9/1992  European Pat. Off. --.

Claim 2, Col. 7, line 22, change "11" to -- 1 --.

Signed and Sealed this

Twenty-first Day of November, 2000

Attest:

Q. TODD DICKINSON

*Attesting Officer*   *Director of Patents and Trademarks*